United States Patent [19]
Meyer

[11] Patent Number: 5,552,368
[45] Date of Patent: Sep. 3, 1996

[54] SULFONYLUREAS

[75] Inventor: Willy Meyer, Riehen, Switzerland

[73] Assignee: Ciba-Geigy Corporation, Tarrytown, N.Y.

[21] Appl. No.: 451,366

[22] Filed: May 26, 1995

Related U.S. Application Data

[62] Division of Ser. No. 419,307, Apr. 10, 1995, which is a continuation of Ser. No. 373,713, Jan. 17, 1995, abandoned, which is a division of Ser. No. 154,768, Nov. 19, 1993, Pat. No. 5,412,107, which is a division of Ser. No. 14,947, Feb. 8, 1993, Pat. No. 5,286,709, which is a division of Ser. No. 823,515, Jan. 21, 1992, Pat. No. 5,209,771.

[30]     Foreign Application Priority Data

Jan. 25, 1991 [CH] Switzerland ............... 220/91-6

[51] Int. Cl.$^6$ ................ A01N 43/653; C07D 249/14
[52] U.S. Cl. ................ 504/211; 548/262.6; 548/263.8
[58] Field of Search .................... 548/262.6; 504/211

[56]           References Cited

U.S. PATENT DOCUMENTS

| | | | |
|---|---|---|---|
| 4,579,584 | 4/1986 | Meyer | 71/93 |
| 4,741,760 | 5/1988 | Meyer | 71/92 |
| 4,892,946 | 1/1990 | Levitte | 544/321 |
| 5,015,284 | 5/1991 | Willms et al. | 504/215 |
| 5,084,082 | 1/1992 | Sebastian | 71/90 |
| 5,127,937 | 7/1992 | Arabori et al. | 504/215 |

FOREIGN PATENT DOCUMENTS

| | | |
|---|---|---|
| 1243674 | 10/1988 | Canada . |
| 0007687 | 2/1980 | European Pat. Off. . |
| 0030138 | 6/1981 | European Pat. Off. . |
| 0073562 | 3/1983 | European Pat. Off. . |
| 0291851 | 11/1988 | European Pat. Off. . |
| 662348 | 9/1987 | Switzerland . |

OTHER PUBLICATIONS

J. Chem. Soc. 2042–2044 (1932).
J. Am. Chem. Soc. 71, 4062–4066 (1949).
Acta Chem. Acamd 28, Series B, 701 (1974).
J. Org. Chem. 48, 2953–2956 (1983).
J. Amer. Chem. Soc., 63, p. 2939 (1941).
J. Amer. Chem. Soc., 101, p. 5317 (1979).
J. Chem. Soc., p. 2126 (1949).
J. Chem. Soc., 3272 (1954).
J. Amer. Chem. Soc., p. 2705 (1956).
Acta Chem. Scand 8, p. 1111 (1954).
J. Org. Chem. 25, p. 1038 (1960).
J. Org. Chem., 38 p. 3986 (1973).
J. Org Chem., 32, p. 4117 (1967).

(List continued on next page.)

Primary Examiner—Patricia L. Morris
Attorney, Agent, or Firm—Edward McC. Roberts

[57]            ABSTRACT

N-Phenylsulfonyl-N'-pyrimidinyl-,-N'-triazinyl-and-N'-triazolylureas and-thioureas of formula I $$\text{(I)} \quad \text{Ar-SO}_2\text{-HN-C(=W)-N(R}_1\text{)-Z}$$

with ortho-substituent $-C(=O)-O-\text{cyclobutyl-}X$ and $R_2$ in which X is oxygen, sulfur, SO or $SO_2$; W is oxygen or sulfur; $R_1$ is hydrogen or methyl;

$R_2$ is hydrogen, fluorine, chlorine, bromine, iodine, $(X)_nR_3$, $NO_2$, $NR_4R_5$, $-C\equiv CR_6$, $$-O-C(R_7)-C\equiv CR_6,$$

or cyano; n is the number 0 or 1; $R_3$, is $C_1$–$C_4$alkyl or $C_1$–$C_4$alkyl which is substituted by 1–4 halogen atoms, $C_1$–$C_3$alkoxy or $C_1$–$C_3$alkylthio; or $C_2$–$C_4$alkenyl or $C_2$–$C_4$alkenyl which is substituted by 1–4 halogen atoms; $R_4$ is hydrogen, $CH_3O$, $CH_3CH_2O$ or $C_1$–$C_3$alkyl; $R_5$ is hydrogen or $C_1$–$C_3$alkyl; $R_6$ is hydrogen, methyl or ethyl; $R_7$ is hydrogen or methyl; Z is Z1: pyrimidine ring with $R_8$, $R_9$, E
Z2: triazine ring with $R_{10}$, $R_{11}$, $R_{12}$
or
Z3: triazole ring with $R_{13}$, $R_{14}$;

E is methine or nitrogen; $R_8$ is $C_1$–$C_4$alkyl, $C_1$–$C_4$alkoxy, $C_1$–$C_4$haloalkoxy, $C_1$–$C_4$haloalkyl, $C_1$–$C_4$haloalkylthio, $C_1$–$C_4$alkylthio, halogen, $C_2$–$C_5$alkoxyalkyl, $C_2$–$C_5$alkoxyalkoxy, amino, $C_1$–$C_3$alkylamino or di($C_1$–$C_3$alkyl)amino; $R_9$ is $C_1$–$C_4$alkyl, $C_1$–$C_4$alkoxy, $C_1$–$C_4$haloalkoxy, $C_1$–$C_4$haloalkylthio, $C_1$–$C_4$alkylthio, $C_2$–$C_5$alkoxyalkyl, $C_2$–$C_5$alkoxyalkoxy, $C_2$–$C_5$alkylthioalkyl or cyclopropyl; $R_{10}$ is hydrogen, fluorine, chlorine, methyl, trifluoromethyl, $CH_3O$, $CH_3CH_2O$, $CH_3S$, $CH_3SO$, $CH_3SO_2$ or cyano; $R_{11}$ is methyl, ethyl, $CH_3O$, $CH_3CH_2O$, fluorine or chlorine; $R_{12}$ is methyl, ethyl, $CH_3O$, $CH_3CH_2O$, fluorine or chlorine; $R_{13}$ is $C_1$–$C_3$alkyl; and $R_{14}$ is $C_1$–$C_3$alkyl, $C_{1–C3}$alkoxy, chlorine or $OCHF_2$; and the salts of these compounds; with the provisos that E is methine if $R_8$ is halogen; and E is methine if $R_8$ or $R_9$ is $OCHF_2$ or $SCHF_2$, and the salts of these compounds with amines, alkali metal or alkaline earth metal bases or quaternary ammonium bases have good pre- and postemergence selective herbicidal and growth-regulating properties.

10 Claims, No Drawings

OTHER PUBLICATIONS

Bull. Chem. Soc. Jpn. 39, 364 (1966).
Bull Chem. Soc. Jpn. 45, 2203 (1972).
J. Chem. Soc C, p. 2334 (1969).
J. Chem. Soc C. p. 2371 (1968).
Synthesis, p. 758 and p. 713 (1978).
Synthesis, p. 264 (1976).
Tetrahedron Lett., p. 3415 (1978).
Tetrahedron Lett. p. 2461 (1969); p. 613 (1976); p. 1121 (1978) and 21, p. 1011 (1978).
Tetrahedron 27, p. 4821 (1971).
J. Med. Chem. 13, p. 1114 (1970).
J. Chem. Soc. Perkin Trans. I, p. 1011 (1978).
Chem. Abstract 70, 46756z (1969).

SULFONYLUREAS

This is a division of Ser. No. 08/419,307 filed Apr. 10, 1995, which is a continuation of Ser. No. 08/373,713, filed Jan. 17, 1995, now abandoned, which is a division of Ser. No. 08/154 768, filed Nov. 19, 1993, now U.S. Pat. No. 5,412,107, which is a division of Ser. No. 08/014,947, filed Feb. 8, 1993, now U.S. Pat. No. 5,286,709, which is a division of Ser. No. 07/823,515, filed Jan. 21, 1992, now U.S. Pat. No. 5,209,771.

The present invention relates to novel, herbicidally active and plant growth-regulating N-phenylsulfonyl-N'-pyrimidinyl-,-N'-triazinyl- and-N'-triazolylureas and-thioureas, processes for their preparation, compositions containing them as active ingredients, and their use for control of weeds, in particular selectively in crops of useful plants, or for regulating and inhibiting plant growth.

Urea compounds, triazine compounds and pyrimidine compounds having a herbicidal action are generally known. Such compounds are described, for example, in European Patent Applications 0 007 687, 0 030 138, 0 073 562 and 0 126 711.

Novel sulfonylureas and-thioureas having herbicidal and plant growth-regulating properties have now been found.

The N-phenylsulfonyl-N'-pyrimidinyl-,-N'-triazinyl- and-N'-triazolylureas and-thioureas according to the invention are those of the formula I

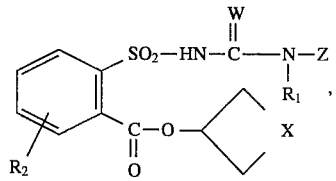

in which X is oxygen, sulfur, SO or $SO_2$; W is oxygen or sulfur; $R_1$ is hydrogen or methyl; $R_2$ is hydrogen, fluorine, chlorine, bromine, iodine, $(X)_nR_3$, $NO_2$, $NR_4R_5$, —C≡$CR_6$,

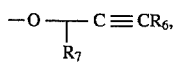

or cyano; n is the number 0 or 1; $R_3$ is $C_1$–$C_4$alkyl or $C_1$–$C_4$alkyl which is substituted by 1–4 halogen atoms, $C_1$–$C_3$alkoxy or $C_1$–$C_3$alkylthio; or $C_2$–$C_4$alkenyl or $C_2$–$C_4$alkenyl which is substituted by 1–4 halogen atoms; $R_4$ is hydrogen, $CH_3O$, $CH_3CH_2O$ or $C_1$–$C_3$alkyl; $R_5$ is hydrogen or $C_1$–$C_3$alkyl; $R_6$ is hydrogen, methy ethyl; $R_7$ is hydrogen or methyl; Z is

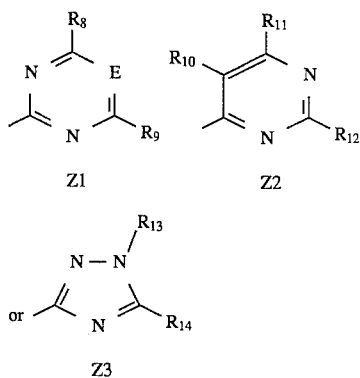

E is methine or nitrogen; $R_8$ is $C_1$–$C_4$alkyl, $C_1$–$C_4$alkoxy, $C_1$–$C_4$haloalkoxy, $C_1$–$C_4$haloalkyl, $C_1$–$C_4$haloalkylthio, $C_1C_4$alkylthio, halogen, $C_2$–$C_5$alkoxyalkyl, $C_2$–$C_5$alkoxyalkoxy, amino, $C_1$–$C_3$alkylamino or di($C_1$–$C_3$alkyl)amino; $R_9$ is $C_1$–$C_4$alkyl, $C_1$–$C_4$alkoxy, $C_{1-C_4}$haloalkoxy, $C_1$–$C_4$haloalkylthio, $C_1$–$C_4$alkylthio, $C_2$–$C_5$alkoxyalkyl, $C_2$–$C_5$alkoxyalkoxy, $C_2$–$C_5$alkylthioalkyl or cyclopropyl; $R_{10}$ is hydrogen, fluorine, chlorine, methyl, trifluoromethyl, $CH_3O$, $CH_3CH_2O$, $CH_3S$, $CH_3SO$, $CH_3SO_2$ or cyano; $R_{11}$ is methyl, ethyl, $CH_3O$, $CH_3CH_2O$, fluorine or chlorine; $R_{12}$ is methyl, ethyl, $CH_3O$, $CH_3CH_2O$, fluorine or chlorine; $R_{13}$ is $C_1$–$C_3$alkyl; and $R_{14}$ is $C_1$–$C_3$alkyl, $C_1$–$C_3$alkoxy, chlorine or $OCHF_2$; and the salts of these compounds; with the provisos that E is methine if $R_8$ is halogen; and E is methine if $R_8$ or $R_9$ is $OCHF_2$ or $SCHF_2$.

In the above definitions, halogen is to be understood as meaning fluorine, chlorine, bromine or iodine, preferably fluorine, chlorine or bromine.

The alkyl groups in the substituent definitions can be straight-chain or branched and are, for example, methyl, ethyl, n-propyl, isopropyl, n-butyl, sec-butyl, isobutyl or tert-butyl. The alkyl groups occurring as or in the substituents preferably have 1–3 carbon atoms. Alkenyl is to be understood as meaning straight-chain or branched alkenyl, for example vinyl, allyl, methallyl, 1-methylvinyl or but-2-en-1-yl. Alkenyl radicals having a chain length of 2 to 3 carbon atoms are preferred.

Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl or 2,2,2-trichloroethyl; preferably trichloromethyl, difluorochloromethyl, trifluoromethyl or dichlorofluoromethyl.

Alkoxy is, for example, methoxy, ethoxy, propyloxy, i-propyloxy, n-butyloxy, isobutyloxy, sec-butyloxy or tert-butyloxy; preferably methoxy or ethoxy.

Haloalkoxy is, for example, difluoromethoxy, trifluoromethoxy, 2,2,2-trifluoroethoxy, 1,1,2,2-tetrafluoroethoxy, 2-fluoroethoxy, 2-chloroethoxy or 2,2-difluoroethoxy; preferably difluoromethoxy, 2-chloroethoxy or trifluoromethoxy.

Alkylthio is, for example, methylthio, ethylthio, propylthio, isopropylthio, n-butylthio, iso-butylthio, sec-butylthio or tert-butylthio, preferably methylthio or ethylthio.

Examples of alkoxyalkoxy are: methoxymethoxy, methoxyethoxy, methoxypropyloxy, ethoxymethoxy, ethoxyethoxy or propyloxymethoxy.

Alkylamino is, for example, methylamino, ethylamino, n-propylamino or isopropylamino. Dialkylamino is, for example, dimethylamino, methylethylamino, diethylamino or n-propylmethylamino.

The invention also relates to the salts which the compounds of the formula I can form with amines, alkali metal and alkaline earth metal bases or quaternary ammonium bases.

Preferred alkali metal and alkaline earth metal hydroxides as salt-forming agents are the hydroxides of lithium, sodium, potassium, magnesium or calcium, in particular those of sodium or potassium.

Examples of amines which are suitable for salt formation are primary, secondary and tertiary aliphatic and aromatic amines, such as methylamine, ethylamine, propylamine, isopropylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, in particular ethyl-, propyl-, diethyl- or triethylamine, especially isopropylamine and diethanolamine.

Examples of quaternary ammonium bases are in general the cations of haloammonium salts, for example the tetramethylammonium cation, the trimethylbenzylammonium cation, the triethylbenzylammonium cation, the tetraethylammonium cation, the trimethylethylammonium cation or even the ammonium cation.

Preferred compounds of the formula I are those in which W is oxygen, Z is preferably Z1, X is oxygen or sulfur, but particularly preferably oxygen, and E is nitrogen.

A preferred group of compounds of the formula I is furthermore that in which Z is Z1 and X is oxygen or sulfur, particularly preferably oxygen, and E is methine.

Compounds of these two groups of compounds of the formula I which are of particular interest are those in which $R_2$ is hydrogen, fluorine, chlorine, $OCH_3$, $OCHF_2$, methyl, $SCH_3$, methoxy, ethoxy or chloroethoxy; $R_8$ is $C_1-C_3$alkyl, $C_1-C_3$alkoxy, $C_1-C_2$haloalkoxy, trifluoromethyl, $CHF_2$, $CH_2F$, $CH_2OCH_3$, fluorine, chlorine, $NH_2$, $NHCH_3$, $N(CH_3)_2$, $SCH_3$ or $CH_2OCH_3$; and $R_9$ is $C_1-C_3$alkyl, $C_1-C_3$alkoxy, $C_1-C_2$haloalkoxy or cyclopropyl.

In particularly preferred compounds of this group, $R_2$ is hydrogen; $R_8$ is methyl, ethyl, $OCH_3$, $OC_2H_5$, $OCHF_2$, $OCH_2CF_3$, chlorine, $NHCH_3$, $N(CH_3)_2$ or $CH_2OCH_3$; and $R_9$ is methyl, $OCH_3$, $OCHF_2$, $OC_2H_5$ or cyclopropyl.

In another preferred sub-group of compounds of the formula I, W is oxygen; Z is Z1; X is sulfur; $R_2$ is hydrogen, fluorine, chlorine, $OCH_3$, $OCHF_2$, methyl or methylthio; $R_8$ is $C_1-C_3$alkyl, $C_1-C_3$alkoxy, $C_1-C_2$haloalkoxy, $CF_3$, $CHF_2$, $CH_2F$, $CH_2OCH_3$, fluorine, chlorine, $NH^2$, $NHCH_3$, $N(CH_3)_2$, $SCH_3$ or $CH_2OCH_3$; and $R_9$ is $C_1-C_3$alkyl, $C_1-C_3$alkoxy, $C_1-C_2$haloalkoxy or cyclopropyl.

Compounds of the formula I from this group which are of interest are those in which W is oxygen; Z is Z1; X is sulfur; $R_2$ is hydrogen; $R_8$ is methyl, ethyl, $OCH_3$, $OC_2H_5$, $OCHF_2$, $OCH_2CF_3$, Cl, $NHCH_3$, $N(CH_3)_2$ or $CH_2OCH_3$; and $R_9$ is methyl, $OCH_3$, $OCHF_2$, $OC_2H_5$ or cyclopropyl.

Preferred individual compounds from the scope of formula I are: N-[2-(oxetan-3-oxycarbonyl)]phenylsulfonyl-N'-(4-methoxy-6-methyl- 1,3,5-triazinyl)-urea; N-[2-(oxetan-3-oxycarbonyl)]phenylsulfonyl-N'-(4,6-dimethylpyrimidin-2-yl)urea; N-[2-(oxetan-3-oxycarbonyl)]phenylsulfonyl-N'-(4-methoxy-6-methylpyrimidin-2-yl)urea; and N-[2-(oxetan-3-oxycarbonyl)]phenylsulfonyl-N'-(4,6-dimethoxypyrimidin-2-yl)urea.

The compounds of the formula I can be prepared by either a) reacting a phenylsulfonamide of the formula II

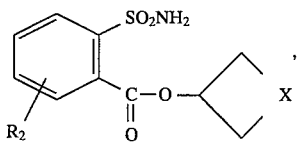

in which $R_2$ and X are as defined under formula I, with an pyrimidinyl-, triazolyl- or triazinylcarbamate or -thiocarbamate of the formula III

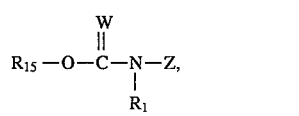

in which W, Z and $R_1$ are as defined under formula I and $R_{15}$ is phenyl or substituted phenyl, in the presence of a base, or b) reacting a sulfonylcarbamate or -thiocarbamate of the formula IV

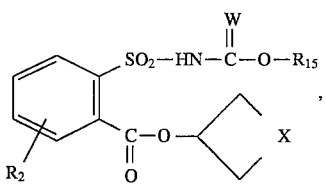

in which $R_2$, W, X and Z are as defined under formula I and $R_{15}$ is as defined under formula III, with an amine of the formula V $$H_2N\text{—}Z \qquad (V)$$

in which Z is as defined under formula I, in the presence of a base, or c) reacting a phenylsulfonamide of the formula II

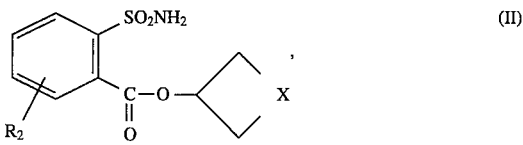

in which $R_2$ and X are as defined under formula I, with an pyrimidinyl-, triazolyl- or triazinyl isocyanate or isothiocyanate of the formula VII $$Y\text{=}N\text{=}C\text{—}Z \qquad (VII)$$

in which Z is as defined under formula I and Y is oxygen or sulfur, in the presence of a base.

Compounds of the formula I can also be prepared by reacting a compound of the formula VIII with a compound of the formula V in the presence of an ammonium-, phosphonium-, sulfonium- or alkali metal cyanate salt of the formula X $$M^+OCN^- \qquad (X)$$

wherein M is an alkali metal or the group $R_{15}R_{16}R_{17}R_{18}Q$, in which $R_{15}R_{16}R_{17}R_{18}$ independently from another is $C_1-C_{18}$-alkyl, benzyl oder phenyl, with the total number of C-atoms not greater than 36; and Q is nitrogen, sulfur or phosphorus. According to this method the compounds N-[2-(oxetan-3-oxycarbonyl)]phenylsulfonyl-N'-(4-methoxy-6-methyl-1,3,5-triazinyl)-urea; N-[2-(oxetan-3-oxycarbonyl)]phenylsulfonyl-N'-(4,6-dimethylpyrimidin-2-yl)urea; N-[2-(oxetan-3-oxycarbonyl)]phenylsulfonyl-N'-(4-methoxy-6-methylpyrimidin-2yl)urea; and N-[2-(oxetan-3-oxycarbonyl)]phenylsulfonyl-N'-(4,6-dimethoxypyrimidin-2-yl)urea can be prepared with advantage. Such reactions are described in Swiss Patent No. 662 348.

The reactions to give compounds of the formula I are advantageously carried out in aprotic, inert organic solvents. Such solvents are hydrocarbons, such as benzene, toluene, xylene or cyclohexane, chlorinated hydrocarbons, such as methylene chloride, chloroform, carbon tetrachloride or chlorobenzene, ethers, such as diethyl ether, ethylene glycol dimethyl ether, diethylene glycol dimethyl ether, tetrahydrofuran or dioxane, nitriles, such as acetonitrile or propionitrile, and amides, such as dimethylformamide, diethylformamide or N-methylpyrrolidone. The reaction temperatures are preferably between −20° and +120° C.

The reactions in general proceed slightly exothermically and can be carried out at room temperature. The mixture is advantageously heated to the boiling point of the reaction mixture for a short time for the purpose of shortening the reaction time or to start the reaction. The reaction times can also be shortened by addition of a few drops of base as a reaction catalyst. Suitable bases are, in particular, tertiary amines, such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as hydrides, such as sodium hydride or calcium hydride, hydroxides, such as sodium hydroxide and potassium hydroxide, carbonates, such as sodium carbonate and potassium carbonate, or bicarbonates, such as potassium bicarbonate and sodium bicarbonate, can also be used as bases.

The end products of the formula I can be isolated by concentrating the mixture and/or evaporating off the solvent and purified by recrystallisation or trituration of the solid residue in solvents in which they are not readily soluble, such as ethers, aromatic hydrocarbons or chlorinated hydrocarbons.

In the preparation processes described above for compounds of the formula I, $R_{15}$ is preferably phenyl which can be substituted by $C_1$–$C_4$alkyl or halogen, especially preferably phenyl.

The phenylsulfonamides of the formula II are novel compounds which have been developed and prepared specifically for the preparation of the active ingredients of the formula I. The present invention thus also relates to them. They can be prepared from the corresponding phenylsulfonyl chlorides of the formula VIII

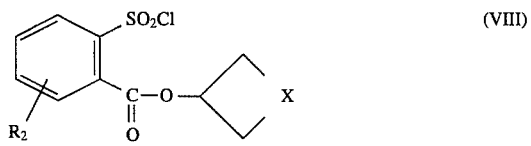

in which $R_2$ and X are as defined under formula I, by reaction with ammonia. Such reactions are known and familiar to the expert.

The phenylsulfonyl chlorides of the formula VIII are novel compounds which have been developed and prepared specifically for the preparation of the active ingredients of the formula I. The present invention therefore likewise relates to them. The phenylsulfonyl chlorides of the formula VIII are prepared by reacting the correspondingly substituted 2-chlorosulfonyl-benzoyl chlorides (cf., for example, D. Davis, Soc. 2042, 2044 (1932)) with a compound of the formula IX

in which X is as defined under formula I, in the presence of a base. Such reactions are known and familiar to the expert.

Phenylsulfonyl chlorides of the formula VIII in which X is oxygen can also be prepared by reacting 2-isopropylthiobenzoic acid (cf., for example, H. Gilman, F. J. Webb, Am. Soc. 71, 4062–4063) with thionyl chloride to give the corresponding benzoyl chloride, which is then convened into the corresponding oxetan-3-yl 2-isopropylthiobenzoate with 3-hydroxyoxetane in the presence of a base, to give finally the sulfonylchloride of the formula VIII by reaction with chlorine. Such reactions are known and familiar to the expert.

Compounds of the formula IX and their preparation are known (cf., for example, B. Lamm et al., Acta Chem. Scand. 28, 701 (1974) or J. Org. Chem. 48, 2953–2956 (1983)).

The sulfonylcarbamates and -thiocarbamates of the formula IV are novel and the present invention relates to them.

They can be obtained, for example, by reaction of the sulfonamides of the formula II with diphenyl carbamate or thiocarbamate in the presence of a base. Such reactions are known and familiar to the expert.

The amines of the formula V are described in European Patent Applications 0 007 687, 0 030 138, 0 073 562 and 0 126 711, and in US Pat. No. 4 579 584.

Processes for the preparation of N-pyrimidinyl- and N-triazinylcarbamates are described, for example, in EP-A-0 101 670. N-Triazolylcarbamates can be prepared analogously.

The active ingredients of the formula I are as a rule employed successfully at rates of application of 0.001 to 2 kg/ha, in particular 0.005 to 1 kg/ha. The doses required for the desired action can be determined by experiments. It depends on the nature of the action, the development stage of the crop plant and of the weed and on the application conditions (location, time, method) and can, as a result of these parameters, be varied within wide ranges.

The compounds of the formula I are distinguished by growth-inhibiting and herbicidal properties which render them excellent for use in crops of useful plants, in particular in cereals, cotton, soya, rape, maize and rice, use in soya crops and cereals being especially preferred. Control of the weeds in soya crops is preferably postemergence. The compounds of the formula I are distinguished in particular by their good degradability.

The invention also relates to herbicidal and plant growth-regulating compositions which comprise a novel active ingredient of the formula I, and methods for inhibition of plant growth.

Plant growth regulators are substances which cause agronomically desirable biochemical and/or physiological and/or morphological changes in/on the plants.

The active ingredients present in the compositions according to the invention influence plant growth in various ways depending on the time of application, dosage, mode of application and environmental conditions. Plant growth regulators of the formula I can, for example, inhibit the vegetative growth of plants. This type of action is of interest on lawn areas, in the growing of ornamentals, in fruit plantations, on road embankments and on sports fields and industrial premises, and also for controlled inhibition of secondary shoots, such as on tobacco. In agriculture, inhibition of the vegetative growth of cereals leads to reduced lodging via strengthening of the stem, and similar agronomic actions are achieved in rape, sunflowers, maize and other crop plants. The number of plants per unit area can moreover be increased by inhibition of the vegetative growth. Another field of use of growth inhibitors is selective control of ground-covering plants in plantations or wide-row crops by severe inhibition of growth, without killing these ground-covering plants, so that competition against the main crop is excluded, but the agronomically positive effects, such as prevention of erosion, nitrogen bonding and loosening of the soil, are retained.

A method for inhibition of plant growth is to be understood as meaning control of the natural plant development without changing, in the sense of mutation, the life-cycle of the plants determined by genetic properties. The method of growth regulation is used at a point in time of the development of the plants which is to be determined in the individual case. The active ingredients of the formula I can be applied before or after emergence of the plants, for example even to the seeds or the seedlings, to roots, tubors, stems, leaves, flowers or other plant parts. This can be effected, for example, by applying the active ingredient itself or in the form of a composition to the plants and/or by treatment of the nutrient medium of the plants (soil).

Various methods and techniques are suitable for use of the compounds of the formula I or compositions containing them for regulating plant growth, for example the following:

i) Seed dressing
  a) Dressing the seeds with an active ingredient formulated as a wettable powder by shaking in a vessel until the active ingredient is distributed uniformly over the seed surface (dry dressing). Up to 4 g of active ingredient of the formula I (in the case of a 50% formulation: up to 8.0 g of wettable powder) are used here per kg of seed.
  b) Dressing of the seeds with an emulsion concentrate of the active ingredient or with an aqueous solution of the active ingredient of the formula I formulated as a wettable powder by method a) (wet dressing).
  c) Dressing by dipping the seed in a mixture containing up to 1000 ppm of active ingredient of the formula I for 1 to 72 hours and if appropriate subsequent drying of the seed (seed soaking).

Dressing of the seed and treatment of the germinated seedling are of course the preferred methods of application, because the treatment with the active ingredient is directed completely toward the target crop. As a rule 0.001 g to 4.0 g of active substance are used per kg of seed, it being possible to deviate upwards or downwards from the limit concentrations stated (repeat dressing) depending on the method, which also allows the addition of other active ingredients or micronutrients.

ii) Controlled release of the active ingredient

The active ingredient is absorbed in solution onto mineral granule carriers or polymerised granules (urea/formaldehyde) and allowed to dry. If appropriate, a coating which allows the active ingredient to be released in metered form over a certain period of time can be applied (coated granules).

The compounds of the formula I are employed in unchanged form, as obtainable from the synthesis, or preferably with the auxiliaries customary in formulation technology, and are therefore processed, for example, to emulsifiable concentrates, directly sprayable or dilutable solutions, dilute emulsions, wettable powders, soluble powders, dusts, granules and also capsules in, for example, polymeric substances in a known manner. The methods of use, such as spraying, misting, dusting, wetting, sprinkling or pouring, are, like the nature of the compositions, chosen according to the effects required and the given circumstances.

The formulations, i.e. the compositions, formulations or preparations comprising the active ingredient of the formula I and if appropriate one or more solid or liquid additives, are prepared in a known manner, for example by intimate mixing and/or grinding of the active ingredients with extenders, for example with solvents, solid carriers and if appropriate surface-active ingredients (surfactants).

Possible solvents are: aromatic hydrocarbons, in particular the fractions $C_8$ to $C_{12}$, such as mixtures of alkylbenzenes, for example xylene mixtures, or alkylated naphthalenes; aliphatic and cycloaliphatic hydrocarbons, such as paraffins, cyclohexane or tetrahydronaphthalene; alcohols, such as ethanol, propanol or butanol; glycols and ethers and esters thereof, such as propylene glycol or dipropylene glycol ether; ketones, such as cyclohexanone, isophorone or diacetone alcohol; strong polar solvents, such as N-methyl-2-pyrrolidone, dimethyl sulfoxide or water;, vegetable oils and esters thereof, such as rape, castor or soya oil; and if appropriate also silicone oils.

Solid carriers which are used, for example for dusts and dispersible powders, are as a rule natural rock powders, such as calcite, talc, kaolin, montmorillonite or attapulgite. Highly disperse silicic acid or highly disperse absorbent polymers can also be added to improve the physical properties. Granular, adsorbent granule carriers are porous types, for example pumice, crushed brick, sepiolite or bentonite, and non-sorbent carder materials are, for example, calcite or sand. A wide range of pregranulated materials of inorganic or organic nature, such as, in particular, dolomite or comminuted plant residues, can moreover be used.

Surface-active ingredients are nonionic, cationic and/or anionic surfactants having good emulsifying, dispersing and wetting properties, depending on the nature of the active ingredient of the formula I to be formulated. Surfactants is also to be understood as meaning surfactant mixtures.

Suitable anionic surfactants can be either so-called water-soluble soaps or water-soluble synthetic surface-active ingredients.

Soaps are the alkali metal, alkaline earth metal or substituted or unsubstituted ammonium salts of higher fatty acids ($C_{10}$–$C_{22}$), for example the sodium or potassium salts of oleic or stearic acid, or of naturally occurring fatty acid mixtures, which can be obtained, for example, from coconut oil or tallow oil. The fatty acid methyltaurine salts may furthermore also be mentioned.

More often, however, so-called synthetic surfactants are used, in particular fatty alcohol sulfonates, fatty alcohol sulfates, sulfonated benzimidazole derivatives or alkylarylsulfonates.

The fatty alcohol sulfonates or sulfates are as a rule in the form of alkali metal, alkaline earth metal or substituted or unsubstituted ammonium salts and contain an alkyl radical having 8 to 22 C atoms, alkyl also including the alkyl moiety of acyl radicals, for example the sodium or calcium salt of ligninsulfonic acid, of dodecylsulfate or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having 8–22 C atoms. Alkylarylsulfonates are, for example, the Na, Ca or triethanolamine salts of dodecylbenzenesulfonic acid, dibutylnaphthalenesulfonic acid or a naphthalenesulfonic acid-formaldehyde condensation product.

Corresponding phosphates, for example salts of the phosphoric acid ester of a p-nonylphenol-(4–14)-ethylene oxide adduct, or phospholipids are furthermore also suitable.

Nonionic surfactants are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble polyethylene oxide adducts, containing 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples of nonionic surfactants are nonylphenol polyethoxyethanols, castor oil polyglycol ether, polypropylene-polyethylene oxide adducts, tributylphenoxypolyethoxyethanol, polyethylene glycol and octylphenoxypolyethoxyethanol.

Fatty acid esters of polyoxyethylenesorbitan, such as polyoxyethylenesorbitan trioleate, are furthermore also suitable.

The cationic surfactants are in particular quaternary ammonium salts which contain at least one alkyl radical having 8 to 22 C atoms as the N-substituent and lower halogenated or unhalogenated alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)ethylammonium bromide.

The surfactants customary in formulation technology are described, inter alia, in the following publications:

"McCutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., N.Y., 1980–1981.

Dr. Helmut Stache "Tensid-Taschenbuch" (Surfactant Handbook), Carler Hanser Verlag, Munich/Vienna 1981.

The pesticidal compositions as a rule comprise 0.1 to 99%, in particular 0.1 to 95%, of active ingredient of the formula I, 1 to 99% of a solid or liquid additive and 0 to 25%, in particular 0.1 to 25%, of a surfactant.

While concentrated compositions are more preferable as commercial goods, the end user as a rule uses dilute compositions.

The compositions can also contain other additives, such as stabilisers, for example epoxidised or unepoxidised vegetable oils (epoxidised coconut oil, rape oil or soya oil), foam suppressants, for example silicone oil, preservatives, viscosity regulators, binders, tackifiers and fertilisers, or other active ingredients to achieve specific effects.

Preferred formulations have, in particular, the following composition: (%=percent by weight)

| Emulsifiable concentrates: | |
|---|---|
| Active ingredient: | 1 to 20% preferably 5 to 10% |
| Surface-active agent: | 5 to 30% preferably 10 to 20% |
| Liquid carrier: | 15 to 94% preferably 70 to 85% |
| Dusts: | |
| Active ingredient: | 0.1 to 10% preferably 0.1 to 1% |
| Solid carrier: | 99.9 to 90% preferably 99.9 to 99% |
| Suspension concentrates: | |
| Active ingredient: | 5 to 75% preferably 10 to 50% |
| Water: | 94 to 24% preferably 88 to 30% |
| Surface-active agent: | 1 to 40%, preferably 2 to 30% |
| Wettable powders: | |
| Active ingredient: | 0.5 to 90% preferably 1 to 80% |
| Surface-active agent: | 0.5 to 20% preferably 1 to 15% |
| Solid carrier: | 5 to 95% preferably 15 to 90% |
| Granules: | |
| Active ingredient: | 0.5 to 30% preferably 3 to 15% |
| Solid carrier: | 99.5 to 70% preferably 97 to 85% |

PREPARATION EXAMPLES

Example H1

2-(Thiaetan-3-Oxycarbonyl)Phenylsulfonyl Chloride

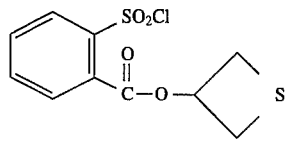

A solution of 52.8 g of 2-chlorosulfonylbenzoyl chloride and 100 ml of absolute toluene is added dropwise to a mixture of 20.7 g of 3-hydroxythiaetan, 20.0 g of pyridine and 250 ml of absolute toluene at a temperature of 0° to 10° C. The reaction mixture is then stirred at a temperature of 20°–25° C. for 2 hours and 300 ml of ice-water are subsequently added. A toluene solution of 2-thiaetanoxycarbonylphenylsulfonyl chloride is obtained by separating off the organic phase, washing it with water and drying it over sodium sulfate, and is employed in Example H2 without further working up.

Example H2

2-(Thiaetan-3-Oxycarbonyl)Phenylsulfonamide

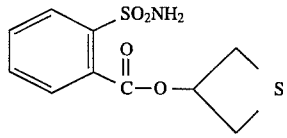

8.5 g of ammonia are passed into a toluene solution of 2-(thiaetan-3-oxycarbonyl)phenylsulfonyl chloride (preparation described in Example H1) in the course of 1 hour. After 400 ml of ice-water has been added to the reaction mixture, the mixture has been filtered and the product has been washed with water and then dried, 9.3 g of 2-thiaetanoxycarbonylphenylsulfonamide having a melting point of 145 to 146° C. are obtained.

Example H3

N-[2-(Thiaetan-3-Oxycarbonyl)Phenylsulfonyl]-N'-(4-Chloro-6-Methoxy- 1,3-Pyrimidin-2-Yl)urea

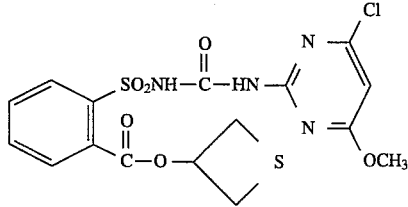

A mixture of 0.69 g of diazabicyclo-[5.4.0]-undec-7-ene (1.5–5) and 5 ml of absolute dioxane is added dropwise to a mixture of 1.23 g of 2-(thiaetan-3-oxycarbonyl)phenylsulfonamide, 1.26 g of 4-chloro-6-methoxy-1,3-pyrimidin-2-yl phenylcarbamate and 20 ml of absolute dioxane and the mixture is then stirred at a temperature of 20° to 25° C. for 4 hours. Pouring the mixture into water, dropwise addition of 10% hydrochloric acid to pH 5, extraction with ethyl acetate, drying of the organic phase, evaporation and crystallisation from ethyl acetate gives 1.15 g of N-[2-( thiaetan- 3-oxycarbonyl)phenylsulfonyl]-N'-(4-chloro-6-methoxy-1,3-pyrimidin-2-yl) urea of melting point 180° to 181 ° C. (decomposition).

Example H4

2-Isopropylthiobenzoyl Chloride

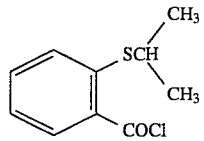

A mixture of 15.7 g of 2-isopropylthiobenzoic acid and 15.7 g of thionyl chloride is heated to the reflux temperature very slowly and kept under reflux until the evolution of gas has ended. 17.3 g of non-purified 2-isopropylsulfonylbenzoyl chloride are obtained as a yellow oil by evaporating off all the excess thionyl chloride.

Example H5

Oxetan-3-yl 2-Isopropylthiobenzoate

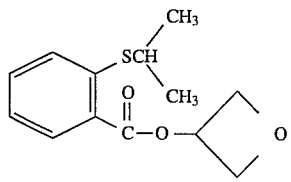

A mixture of 12.9 g of 2-isopropylthiobenzoyl chloride and 20 ml of absolute toluene is added dropwise to a mixture of 4.44 g of 3-hydroxyoxetane, 6.64 g of pyridine and 60 ml of absolute toluene at a temperature of 15° to 20° C. The suspension formed is stirred at a temperature of 20°–25° C. for 2 hours and at a temperature of 40°–45° C. for a further 3 hours. Adding water to the reaction mixture, washing the organic phase with water and drying and evaporating it gives 12.6 g of oxetan-3-yl 2-isopropylthiobenzoate as a pale yellow oil.

Example H6

2-(Oxetan-3-Oxycarbonyl)Phenylsulfonyl Chloride

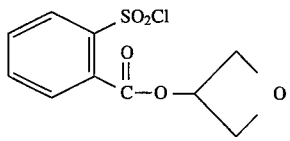

11.2 g of chlorine are passed into a mixture of 12.6 g of oxetan-3-yl 2-isopropylthiobenzoate, 12.9 g of sodium acetate and 100 ml of 50% acetic acid at a temperature of −5° to 0° C. in the course of 1 hour, and the mixture is then stirred at a temperature of 0° C. for 15 minutes. By adding methylene chloride to the reaction mixture, washing the organic phase with ice-water and drying it, a methylene chloride solution of 2-(oxetan-3-oxycarbonyl)-phenylsulfonyl chloride is obtained, which is employed in Example H7 without further purification.

Example H7

2-(Oxetan-3-Oxycarbonyl)Phenylsulfonamide

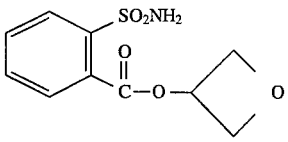

2.5 g of ammonia are passed into a methylene chloride solution of 2-(oxetan-3-oxycarbonyl)phenylsulfonyl chloride (Example H6) at a temperature of 0° to 5° C. in the course of 45 minutes. By adding water to the reaction mixture, washing the organic phase with water, drying and evaporating it and crystallising the residue from a methylene chloride/diethyl ether mixture, 6.7 g of 2-(oxetan-3-oxycarbonyl)phenylsulfonamide of melting point 169° to 170° C. are obtained.

Example H8

N-[2-(Oxetan-3-Oxycarbonyl)Phenylsulfonyl]-N'-(4-Methoxy-6-Methyl-1,3,5-Triazinyl)Urea (Compound No. 3.011)

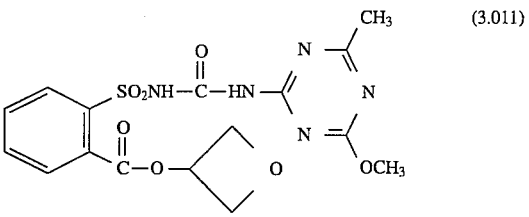

A mixture of 1.52 g of diazabicyclo-[5.4.0]-undec-7-ene(1.5-5) and 5 ml of absolute dioxane is added dropwise to a mixture of 2.57 g of 2-(oxetan-3-oxycarbonyl)phenylsulfonamide, 2.6 g of 4-methoxy-6-methyl-1,3,5-triazinyl phenylcarbamate and 40 ml of absolute dioxane at 20°–25° C., and the mixture is then stirred at a temperature of 20° to 25° C. for 4 hours. By adding to water, dropwise addition of 10% hydrochloric acid to establish a pH of 5, extraction with ethyl acetate, drying of the organic phase, evaporation and crystallisation from ethyl acetate, 2.8 g of N-[2-(oxetan-3-oxycarbonyl)phenylsulfonyl]-N'-(4-methoxy-6-methyl-1,3,5-triazinyl)-urea (compound No. 3.011) of melting point 162° to 163° C. (decomposition) are obtained.

Example H9

Phenyl N-[2-(Oxetan-3-Oxycarbonyl)Phenylsulfonyl]carbamate(compound No. 1.030)

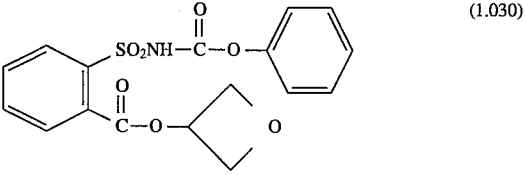

A mixture of 2.57 g of 2-(oxetan-3-oxycarbonyl)phenylsulfonamide, 2.14 g of diphenyl carbonate, 1.38 g of potassium carbonate and 13 ml of dimethylformamide is stirred at a temperature of 20°–25° C. for 15 hours. The reaction mixture is then poured into ice-water, the pH is brought to a value of 5–6 by dropwise addition of 10% hydrochloric acid and the mixture is extracted with ethyl acetate and washed with water. After drying over sodium sulfate, evaporation and crystallisation of the residue from diethyl ether, 2.2 g of phenyl N-[2-(oxetan-3-oxycarbonyl)phenylsulfonyl]carbamate (compound 1.030) of melting point 91°–92° C. are obtained.

Example H10

N-[2-(Oxetan-3-Oxycarbonyl)Phenylsulfonyl]N'-[4-Methoxy-6-(2,2,2-Trifluoroethoxy) pyrimidin-2-yl]urea- (compound No. 2.034)

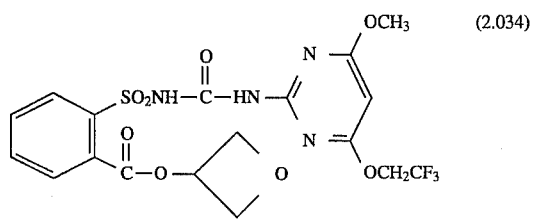

A mixture of 0.75 g of phenyl N-[2-(oxetan-3-oxycarbonyl)phenylsulfonyl]carbamate, 0.34 g of 2-amino-4-methoxy-6-(2,2,2-trifluoroethoxy)pyrimidine and 7 ml of dioxane is stirred at a temperature of 90°–95° C. for 4 hours. After the reaction mixture has been evaporated and the residue crystallised from acetone, 0.7 g of N-[2-(oxetan-3-oxycarbonyl)phenylsulfonyl]-N'-[4-methoxy-6-(2,2,2-trifluoroethoxy) pyrimidin-2-yl]urea (compound No. 2.034) of melting point 185°–186° C. is obtained.

The compounds of the formula I listed in the attached tables and intermediates thereof are prepared in an analogous manner.

TABLE 1

Intermediates of the formula

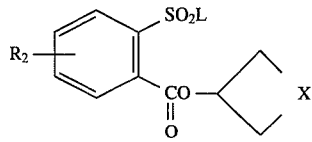

| Compound No. | $R_2$ | L | X | Melting point [°C.] |
|---|---|---|---|---|
| 1.001 | H | Cl | O | oil |
| 1.002 | H | Cl | S | oil |
| 1.003 | H | $NH_2$ | O | 169–170° |
| 1.004 | H | $NH_2$ | S | 145–146° |
| 1.005 | H | $NH_2$ | SO | |
| 1.006 | H | $NH_2$ | $SO_2$ | 213–214° |
| 1.007 | 5-F | $NH_2$ | O | |
| 1.008 | 5-F | $NH_2$ | S | |
| 1.009 | 5-$CF_3$ | $NH_2$ | O | |
| 1.010 | 5-Cl | $NH_2$ | O | |
| 1.011 | 5-$OCH_3$ | $NH_2$ | O | |
| 1.012 | 5-$CH_2CH_2CF_3$ | $NH_2$ | O | |
| 1.013 | 5-$OCH_2CH_2Cl$ | $NH_2$ | O | |
| 1.014 | 5-$OCHF_2$ | $NH_2$ | O | |
| 1.015 | 5-$OCH_2CH_2OCH_3$ | $NH_2$ | O | |
| 1.016 | 5-$CH_3$ | $NH_2$ | O | |
| 1.017 | 5-$OCH_2CH=CH_2$ | $NH_2$ | O | |
| 1.018 | 6-Cl | $NH_2$ | O | |
| 1.019 | 6-F | $NH_2$ | O | |
| 1.020 | 3-Cl | $NH_2$ | O | |
| 1.021 | 3-F | $NH_2$ | O | |
| 1.022 | 5-$NO_2$ | $NH_2$ | O | |
| 1.023 | 5-C≡CH | $NH_2$ | O | |
| 1.024 | 5-CH=CH-$CF_3$ | $NH_2$ | O | |
| 1.025 | 5-$CH_2$-C≡CH | $NH_2$ | O | |
| 1.026 | 5-CN | $NH_2$ | O | |
| 1.027 | 5-$N(CH_3)_2$ | $NH_2$ | O | |
| 1.028 | 5-$SCH_2CHF_2$ | $NH_2$ | O | |
| 1.029 | H | —NH—C(=O)—O—⟨C6H4⟩—$CH_3$ | O | |

TABLE 1-continued
Intermediates of the formula
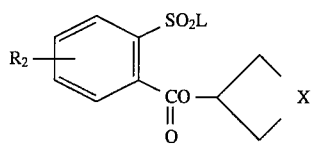
| Compound No. | $R_2$ | L | X | Melting point [°C.] |
|---|---|---|---|---|
| 1.030 | H | —NH—C(=O)—O—C₆H₅ | O | 91–92° |
| 1.031 | 5-F | —NH—C(=O)—O—C₆H₅ | O | |
| 1.032 | 4-F | —NH—C(=O)—O—C₆H₅ | O | |
| 1.033 | 4-F | Cl | O | |
| 1.034 | 4-F | $NH_2$ | O | |
| 1.035 | 4-OCH₃ | Cl | O | |
| 1.036 | 4-OCH₃ | $NH_2$ | O | |
| 1.037 | 4-OCH₃ | —NH—C(=O)—O—C₆H₅ | O | |
| 1.038 | 5-OCH₃ | $NH_2$ | O | |
| 1.039 | 5-OCH₃ | —NH—C(=O)—O—C₆H₅ | O | |
| 1.040 | 6-CH₃ | $NH_2$ | O | |
| 1.041 | 6-Cl | —NH—C(=O)—O—C₆H₅ | O | |
| 1.042 | 5-C≡C—CH₃ | —NH—C(=O)—O—C₆H₅ | O | |
| 1.043 | 5-C≡C—CH₃ | $NH_2$ | O | |

TABLE 2

Compounds of the formula Ia

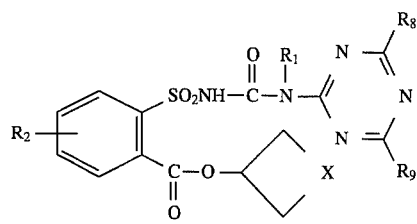

| Comp. No. | $R_1$ | $R_2$ | $R_8$ | $R_9$ | X | m.p. [°C.] |
|---|---|---|---|---|---|---|
| 2.001 | H | H | $CH_3$ | $CH_3$ | O | 161–162° |
| 2.002 | H | H | $CH_3$ | $OCH_3$ | O | 153–155° (decomposition) |
| 2.003 | H | H | $OCH_3$ | $OCH_3$ | O | 166–167° |
| 2.004 | H | H | $OCH_3$ | $OCHF_2$ | O | 181–183° |
| 2.005 | H | H | $CH_3$ | $OC_2H_5$ | O | |
| 2.006 | H | H | $OCH_3$ | $OC_2H_5$ | O | |
| 2.007 | H | H | $CH_3$ | $OCHF_2$ | O | 165–167° |
| 2.008 | H | H | $OCHF_2$ | $OCHF_2$ | O | 164–166° |
| 2.009 | H | H | $OCH_3$ | ◁ | O | |
| 2.010 | H | H | $OC_2H_5$ | $OCHF_2$ | O | |
| 2.011 | H | H | $CH_3$ | $SCHF_2$ | O | |
| 2.012 | H | H | Cl | $OCH_3$ | O | 175–177° (decomposition) |
| 2.013 | H | H | Cl | $OCHF_2$ | O | |
| 2.014 | H | H | Cl | $SCHF_2$ | O | |
| 2.015 | H | H | $CH_2Cl$ | $CH_3$ | O | |
| 2.016 | H | H | $CH_2Cl$ | $OCH_3$ | O | |
| 2.017 | H | H | $CH_2OCH_3$ | $OCH_3$ | O | |
| 2.018 | H | H | $CH_3$ | $SCH_3$ | O | |
| 2.019 | H | H | $OCH_3$ | $SCH_3$ | O | |
| 2.020 | H | H | Cl | $SCH_3$ | O | |
| 2.021 | H | H | $HN-CH_3$ | $CH_3$ | O | |
| 2.022 | H | H | $HN-CH_3$ | $OCH_3$ | O | |
| 2.023 | H | H | $HN-CH_3$ | $OC_2H_5$ | O | |
| 2.024 | H | H | $N(CH_3)_2$ | $CH_3$ | O | |
| 2.025 | H | H | $N(CH_3)_2$ | $OCH_3$ | O | |
| 2.026 | H | H | $OC_2H_5$ | $OCH_3$ | O | |
| 2.027 | H | H | $OC_2H_5$ | $C_2H_5$ | O | |
| 2.028 | H | H | $N(CH_3)_2$ | $OCHF_2$ | O | |
| 2.029 | H | H | $CH_2SCH_3$ | $OCH_3$ | O | |
| 2.030 | H | H | $CH_2F$ | $OCH_3$ | O | |
| 2.031 | H | H | F | $OCH_3$ | O | |
| 2.032 | H | H | $OC_2H_5$ | $OC_2H_5$ | O | |
| 2.033 | H | H | $CH_3$ | $OCH_2CF_3$ | O | |
| 2.034 | H | H | $OCH_3$ | $OCH_2CF_3$ | O | 185–186° |
| 2.035 | H | H | $N(CH_3)_2$ | $OCH_2CF_3$ | O | |
| 2.036 | H | H | $OCH_3$ | $OC_3H_7(i)$ | O | |
| 2.037 | H | H | $CF_3$ | $CH_3$ | O | |
| 2.038 | H | H | $CF_3$ | $OCH_3$ | O | |
| 2.039 | H | H | $CF_3$ | $OC_2H_5$ | O | |
| 2.040 | H | H | Cl | $CH_3$ | O | |
| 2.041 | H | H | Cl | $CF_3$ | O | |
| 2.042 | H | H | Cl | $OCH_2CF_3$ | O | |
| 2.043 | $CH_3$ | H | $CH_3$ | $OCH_3$ | O | |
| 2.044 | $CH_3$ | H | Cl | $OCH_3$ | O | |
| 2.045 | $CH_3$ | H | $OCH_3$ | $OCH_3$ | O | |
| 2.046 | $CH_3$ | H | $CH_3$ | $CH_3$ | O | |
| 2.047 | H | 5-Cl | $CH_3$ | $OCH_3$ | O | |
| 2.048 | H | 5-F | $CH_3$ | $OCH_3$ | O | |
| 2.049 | H | 6-Cl | $CH_3$ | $OCH_3$ | O | |
| 2.050 | H | 6-F | $CH_3$ | $OCH_3$ | O | |
| 2.051 | H | 5-$CF_3$ | $CH_3$ | $OCH_3$ | O | |
| 2.052 | H | 5-$OCH_3$ | $CH_3$ | $OCH_3$ | O | |
| 2.053 | H | 5-$NO_2$ | $CH_3$ | $OCH_3$ | O | |
| 2.054 | H | 3-Cl | $CH_3$ | $OCH_3$ | O | |
| 2.055 | H | 3-F | $CH_3$ | $OCH_3$ | O | |
| 2.056 | H | 5-C≡CH | $CH_3$ | $OCH_3$ | O | |
| 2.057 | H | 5-CH=CH-$CF_3$ | $CH_3$ | $OCH_3$ | O | |

TABLE 2-continued

Compounds of the formula Ia

(Ia)

| Comp. No. | $R_1$ | $R_2$ | $R_8$ | $R_9$ | X | m.p. [°C.] |
|---|---|---|---|---|---|---|
| 2.058 | H | 5-CH$_3$ | CH$_3$ | OCH$_3$ | O | |
| 2.059 | H | 5-OCH$_2$CH$_2$Cl | CH$_3$ | OCH$_3$ | O | |
| 2.060 | H | 5-OCHF$_2$ | CH$_3$ | OCH$_3$ | O | |
| 2.061 | H | 5-OCH$_2$CH=CH$_2$ | CH$_3$ | OCH$_3$ | O | |
| 2.062 | H | 5-OCH$_2$C≡CH | CH$_3$ | OCH$_3$ | O | |
| 2.063 | H | 5-CN | CH$_3$ | OCH$_3$ | O | |
| 2.064 | H | 5-N(CH$_3$)$_2$ | CH$_3$ | OCH$_3$ | O | |
| 2.065 | H | 5-CH$_2$CH$_2$CF$_3$ | CH$_3$ | OCH$_3$ | O | |
| 2.066 | H | 5-OCH$_2$CH$_2$OCH$_3$ | CH$_3$ | OCH$_3$ | O | |
| 2.067 | H | 5-SCH$_2$CHF$_2$ | CH$_3$ | OCH$_3$ | O | |
| 2.068 | H | H | OC$_2$H$_5$ |  | O | |
| 2.069 | H | H | C$_3$H$_7$(i) | OCH$_3$ | O | |
| 2.070 | H | H | NH$_2$ | OCH$_3$ | O | |
| 2.071 | H | H | OCH$_3$ | SCH$_2$CF$_3$ | O | |
| 2.072 | H | H | OCH$_3$ | OCH$_2$CH$_3$OCH$_3$ | O | |
| 2.073 | H | H | F | OCHF$_2$ | O | |
| 2.074 | H | 5-Cl | Cl | OCH$_3$ | O | |
| 2.075 | H | 5-F | Cl | OCH$_3$ | O | |
| 2.076 | H | 5-CF$_3$ | Cl | OCH$_3$ | O | |
| 2.077 | H | 5-CH$_3$ | Cl | OCH$_3$ | O | |
| 2.078 | H | 5-OCH$_3$ | Cl | OCH$_3$ | O | |
| 2.079 | H | 5-F | CH$_3$ | CH$_3$ | O | |
| 2.080 | H | 5-F | OCH$_3$ | OCH$_3$ | O | |
| 2.081 | H | 5-OCHF$_2$ | Cl | OCH$_3$ | O | |
| 2.082 | H | H | CH$_3$ | CH$_3$ | S | 172–174° (decomposition) |
| 2.083 | H | H | CH$_3$ | OCH$_3$ | S | 176–177° (decomposition) |
| 2.084 | H | H | OCH$_3$ | OCH$_3$ | S | 187–188° (decomposition) |
| 2.085 | H | H | OCH$_3$ | OCHF$_2$ | S | |
| 2.086 | H | H | CH$_3$ | OC$_2$H$_5$ | S | |
| 2.087 | H | H | OCH$_3$ | OC$_2$H$_5$ | S | |
| 2.088 | H | H | CH$_3$ | OCHF$_2$ | S | |
| 2.089 | H | H | OCHF$_2$ | OCHF$_2$ | S | |
| 2.090 | H | H | OCH$_3$ |  | S | |
| 2.091 | H | H | OC$_2$H$_5$ | OCHF$_2$ | S | |
| 2.092 | H | H | CH$_3$ | SCHF$_2$ | S | |
| 2.093 | H | H | Cl | OCH$_3$ | S | 180–181° (decomposition) |
| 2.094 | H | H | Cl | OCHF$_2$ | S | |
| 2.095 | H | H | Cl | SCHF$_2$ | S | |
| 2.096 | H | H | CH$_2$Cl | CH$_3$ | S | |
| 2.097 | H | H | CH$_2$Cl | OCH$_3$ | S | |
| 2.098 | H | H | CH$_2$OCH$_3$ | OCH$_3$ | S | |
| 2.099 | H | H | CH$_3$ | SCH$_3$ | S | |
| 2.100 | H | H | OCH$_3$ | SCH$_3$ | S | |
| 2.101 | H | H | Cl | SCH$_3$ | S | |
| 2.102 | H | H | HN—CH$_3$ | CH$_3$ | S | |
| 2.103 | H | H | HN—CH$_3$ | OCH$_3$ | S | |
| 2.104 | H | H | HN—CH$_3$ | OC$_2$H$_5$ | S | |
| 2.105 | H | H | N(CH$_3$)$_2$ | CH$_3$ | S | |
| 2.106 | H | H | N(CH$_3$)$_2$ | OCH$_3$ | S | |
| 2.107 | H | H | C$_2$H$_5$ | OCH$_3$ | S | |
| 2.108 | H | H | C$_2$H$_5$ | OC$_2$H$_5$ | S | |
| 2.109 | H | H | N(CH$_3$)$_2$ | OCHF$_2$ | S | |

TABLE 2-continued

Compounds of the formula Ia

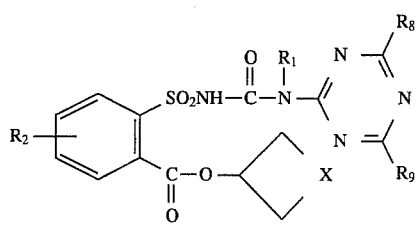

(Ia)

| Comp. No. | $R_1$ | $R_2$ | $R_8$ | $R_9$ | X | m.p. [°C.] |
|---|---|---|---|---|---|---|
| 2.110 | H | H | $CH_2SCH_3$ | $OCH_3$ | S | |
| 2.111 | H | H | $CH_2F$ | $OCH_3$ | S | |
| 2.112 | H | H | F | $OCH_3$ | S | |
| 2.113 | H | H | $OC_2H_5$ | $OC_2H_5$ | S | |
| 2.114 | H | H | $CH_3$ | $OCH_2CF_3$ | S | |
| 2.115 | H | H | $OCH_3$ | $OCH_2CF_3$ | S | |
| 2.116 | H | H | $N(CH_3)_2$ | $OCH_2CF_3$ | S | |
| 2.117 | H | H | $OCH_3$ | $OC_3H_7(i)$ | S | |
| 2.118 | H | H | $CF_3$ | $CH_3$ | S | |
| 2.119 | H | H | $CF_3$ | $OC_2H_5$ | S | |
| 2.120 | H | H | Cl | $CH_3$ | S | |
| 2.121 | H | H | Cl | $CF_3$ | S | |
| 2.122 | H | H | Cl | $OCH_2CF_3$ | S | |
| 2.123 | $CH_3$ | H | $CH_3$ | $OCH_3$ | S | |
| 2.124 | $CH_3$ | H | Cl | $OCH_3$ | S | |
| 2.125 | $CH_3$ | H | $OCH_3$ | $OCH_3$ | S | |
| 2.126 | $CH_3$ | H | $CH_3$ | $CH_3$ | S | |
| 2.127 | H | 5-Cl | $CH_3$ | $OCH_3$ | S | |
| 2.128 | H | 5-F | $CH_3$ | $OCH_3$ | S | |
| 2.129 | H | 6-Cl | $CH_3$ | $OCH_3$ | S | |
| 2.130 | H | 6-F | $CH_3$ | $OCH_3$ | S | |
| 2.131 | H | 5-$CF_3$ | $CH_3$ | $OCH_3$ | S | |
| 2.132 | H | 5-$OCH_3$ | $CH_3$ | $OCH_3$ | S | |
| 2.133 | H | 5-$NO_2$ | $CH_3$ | $OCH_3$ | S | |
| 2.134 | H | H | $CF_3$ | $OCH_3$ | S | |
| 2.135 | H | H | $CH_3$ | $CH_3$ | SO | |
| 2.136 | H | H | $CH_3$ | $OCH_3$ | SO | |
| 2.137 | H | H | Cl | $OCH_3$ | SO | |
| 2.138 | H | H | $OCH_3$ | $OCH_3$ | SO | |
| 2.139 | H | H | $CH_3$ | $CH_3$ | $SO_2$ | |
| 2.140 | H | H | $CH_3$ | $OCH_3$ | $SO_2$ | |
| 2.141 | H | H | Cl | $OCH_3$ | $SO_2$ | |
| 2.142 | H | H | $OCH_3$ | $OCH_3$ | $SO_2$ | 160–161° (decomposition) |
| 2.143 | H | H | $OC_2H_5$ | ◁ | S | |
| 2.144 | H | H | $C_3H_7$ | $OCH_3$ | S | |
| 2.145 | H | H | $NH_2$ | $OCH_3$ | S | |
| 2.146 | H | H | $OCH_3$ | $SCH_2CF_3$ | S | |
| 2.147 | H | H | $OCH_3$ | $OCH_2CH_2OCH_3$ | S | |
| 2.148 | H | H | F | $OCHF_2$ | S | |
| 2.149 | H | 3-Cl | $CH_3$ | $OCH_3$ | S | |
| 2.150 | H | 3-Cl | Cl | $OCH_3$ | S | |
| 2.151 | H | 3-F | $CH_3$ | $OCH_3$ | S | |
| 2.152 | H | 3-F | Cl | $OCH_3$ | S | |
| 2.153 | H | 5-C≡CH | $CH_3$ | $OCH_3$ | S | |
| 2.154 | H | 5-CH=CH-$CF_3$ | $CH_3$ | $OCH_3$ | S | |
| 2.155 | H | 5-$CH_3$ | $CH_3$ | $OCH_3$ | S | |
| 2.156 | H | 5-$OCH_2CH_2Cl$ | $CH_3$ | $OCH_3$ | S | |
| 2.157 | H | 5-$OCHF_2$ | $CH_3$ | $OCH_3$ | S | |
| 2.158 | H | 5-$OCH_2CH=CH_2$ | $CH_3$ | $OCH_3$ | S | |
| 2.159 | H | 5-$OCH_2C≡CH$ | $CH_3$ | $OCH_3$ | S | |
| 2.160 | H | 5-$CH_2CH_2CF_3$ | $CH_3$ | $OCH_3$ | S | |
| 2.161 | H | 5-$OCH_2CH_2OCH_3$ | $CH_3$ | $OCH_3$ | S | |
| 2.162 | H | 5-$SCH_2CHF_2$ | $CH_3$ | $OCH_3$ | S | |
| 2.163 | H | 6-$CH_3$ | $N(CH_3)_2$ | $OCH_2CF_3$ | O | |
| 2.164 | H | 5-$OCH_2CH_2Cl$ | $CH_3$ | $CH_3$ | O | |
| 2.165 | H | 5-$OCH_2CH_2Cl$ | $OCH_3$ | $OCH_3$ | O | |

TABLE 2-continued

Compounds of the formula Ia

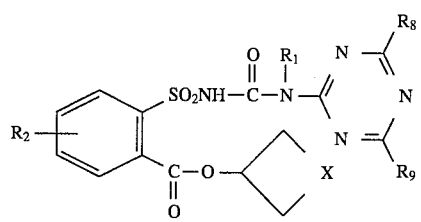

(Ia)

| Comp. No. | $R_1$ | $R_2$ | $R_8$ | $R_9$ | X | m.p. [°C.] |
|---|---|---|---|---|---|---|
| 2.166 | H | 5-C≡CCH$_3$ | OCH$_3$ | OCH$_3$ | O | |
| 2.167 | H | 5-C≡CCH$_3$ | OCH$_3$ | CH$_3$ | O | |
| 2.168 | H | 5-C≡CCH$_3$ | CH$_3$ | CH$_3$ | O | |
| 2.169 | H | 4-F | CH$_3$ | CH$_3$ | O | |
| 2.170 | H | 4-F | OCH$_3$ | CH$_3$ | O | |
| 2.171 | H | 4-OCH$_3$ | OCH$_3$ | CH$_3$ | O | |
| 2.172 | H | 4-OCH$_3$ | CH$_3$ | CH$_3$ | O | |
| 2.173 | H | 5-C≡CH | CH$_3$ | | O | |
| 2.174 | H | 5-C≡CH | OCH$_3$ | CH$_3$ | O | |
| 2.175 | H | 5-C≡CH | OCH$_3$ | OCH$_3$ | O | |
| 2.176 | H | 6-CH$_2$F | OCH$_3$ | OCH$_3$ | O | |
| 2.177 | H | 6-CH$_2$F | CH$_3$ | CH$_3$ | O | |
| 2.178 | H | 6-CH$_2$F | CH$_3$ | OCH$_3$ | O | |
| 2.179 | H | 5-CH$_2$CH$_3$ | CH$_3$ | OCH$_3$ | O | |
| 2.180 | H | 5-CH$_2$CH$_3$ | CH$_3$ | CH$_3$ | O | |

TABLE 3

Compounds of the formula Ib:

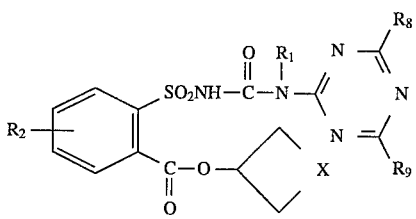

(Ib)

| Comp. No. | $R_1$ | $R_2$ | $R_8$ | $R_9$ | X | m.p. [°C.] |
|---|---|---|---|---|---|---|
| 3.001 | H | H | CH$_3$ | CH$_3$ | O | |
| 3.002 | H | H | CH$_3$ | SCH$_3$ | O | |
| 3.003 | H | H | OCH$_3$ | OCH$_3$ | O | 185–187° (decomposition) |
| 3.004 | H | H | CH$_3$ | OC$_2$H$_5$ | O | 158–160° |
| 3.005 | H | H | OCH$_3$ | OC$_2$H$_5$ | O | |
| 3.006 | H | H | OCH$_3$ | ◁ | O | 154–156° |
| 3.007 | H | H | CH$_2$Cl | OCH$_3$ | O | |
| 3.008 | H | H | CH$_2$OCH$_3$ | OCH$_3$ | O | |
| 3.009 | H | H | CH$_2$SCH$_3$ | OCH$_3$ | O | |
| 3.010 | H | H | OC$_2$H$_5$ | OC$_2$H$_5$ | O | |
| 3.011 | H | H | CH$_3$ | OCH$_3$ | O | 162–163° (decomposition) |
| 3.012 | H | H | OCH$_3$ | SCH$_3$ | O | |
| 3.013 | H | H | OCH$_3$ | OC$_3$H$_7$(i) | O | |
| 3.014 | H | H | HN—CH$_3$ | CH$_3$ | O | |
| 3.015 | H | H | HN—CH$_3$ | OCH$_3$ | O | |
| 3.016 | H | H | HN—CH$_3$ | OC$_2$H$_5$ | O | |
| 3.017 | H | H | N(CH$_3$)$_2$ | CH$_3$ | O | |

TABLE 3-continued

Compounds of the formula Ib:

(Ib)

| Comp. No. | $R_1$ | $R_2$ | $R_8$ | $R_9$ | X | m.p. [°C.] |
|---|---|---|---|---|---|---|
| 3.018 | H | H | $N(CH_3)_2$ | $OCH_3$ | O | 169–170° (decomposition) |
| 3.019 | H | H | $C_2H_5$ | $OCH_3$ | O | 169–171° (decomposition) |
| 3.020 | H | H | $CH_2F$ | $OCH_3$ | O | |
| 3.021 | H | H | $CH_3$ | $OCH_2CF_3$ | O | |
| 3.022 | H | H | $OCH_3$ | $OCH_2CF_3$ | O | 180–182° |
| 3.023 | H | H | $N(CH_3)_2$ | $OCH_2CF_3$ | O | 177–178° |
| 3.024 | H | H | $CF_3$ | $OCH_3$ | O | |
| 3.025 | H | H | $OCH_3$ | $OCH_2CH_2OCH_3$ | O | |
| 3.026 | $CH_3$ | H | $CH_3$ | $OCH_3$ | O | |
| 3.027 | $CH_3$ | H | $OCH_3$ | $OCH_3$ | O | |
| 3.028 | H | 5-Cl | $CH_3$ | $OCH_3$ | O | |
| 3.029 | H | 5-F | $CH_3$ | $OCH_3$ | O | |
| 3.030 | H | 6-Cl | $CH_3$ | $OCH_3$ | O | |
| 3.031 | H | 6-F | $CH_3$ | $OCH_3$ | O | |
| 3.032 | H | $5-CF_3$ | $CH_3$ | $OCH_3$ | O | |
| 3.033 | H | $5-OCH_3$ | $CH_3$ | $OCH_3$ | O | |
| 3.034 | H | $5-NO_2$ | $CH_3$ | $OCH_3$ | O | |
| 3.035 | H | $5-C\equiv C-CH$ | $CH_3$ | $OCH_3$ | O | |
| 3.036 | H | $5-CH=CH-CF_3$ | $CH_3$ | $OCH_3$ | O | |
| 3.037 | H | $5-CH_3$ | $CH_3$ | $OCH_3$ | O | |
| 3.038 | H | $5-OCH_2CH_2Cl$ | $CH_3$ | $OCH_3$ | O | |
| 3.039 | H | $5-OCHF_2$ | $CH_3$ | $OCH_3$ | O | |
| 3.040 | H | 3-Cl | $CH_3$ | $OCH_3$ | O | |
| 3.041 | H | 3-F | $CH_3$ | $OCH_3$ | O | |
| 3.042 | H | H | $OC_2H_5$ |  | O | 152–153° |
| 3.043 | H | H | $C_3H_7(i)$ | $OCH_3$ | O | |
| 3.044 | H | H | $OCH_3$ | $SCH_2CF_3$ | O | |
| 3.045 | H | H | $NH_2$ | $OCH_3$ | O | |
| 3.046 | H | $5-OCH_2CH=CH_2$ | $CH_3$ | $OCH_3$ | O | |
| 3.047 | H | $5-OCH_2C\equiv CH$ | $CH_3$ | $OCH_3$ | O | |
| 3.048 | H | 5-CN | $CH_3$ | $OCH_3$ | O | |
| 3.049 | H | $5-N(CH_3)_2$ | $CH_3$ | $OCH_3$ | O | |
| 3.050 | H | $5-CH_2-CH_2-CF_3$ | $CH_3$ | $OCH_3$ | O | |
| 3.051 | H | $5-OCH_2CH_2OCH_3$ | $CH_3$ | $OCH_3$ | O | |
| 3.052 | H | $5-SCH_2CHF_2$ | $CH_3$ | $OCH_3$ | O | |
| 3.053 | H | H | $CH_3$ | $OCH_3$ | S | 164–165° (decomposition) |
| 3.054 | H | H | $CH_3$ | $CH_3$ | S | |
| 3.055 | H | H | $OCH_3$ | $OCH_3$ | S | |
| 3.056 | H | H | $CH_3$ | $OC_2H_5$ | S | |
| 3.057 | H | H | $OCH_3$ | $OC_2H_5$ | S | |
| 3.058 | H | H | $OCH_3$ |  | S | |
| 3.059 | H | H | $CH_2Cl$ | $OCH_3$ | S | |
| 3.060 | H | H | $CH_2OCH_3$ | $OCH_3$ | S | |
| 3.061 | H | H | $CH_2SCH_3$ | $OCH_3$ | S | |
| 3.062 | H | H | $OC_2H_5$ | $OC_2H_5$ | S | |
| 3.063 | H | H | $CH_3$ | $SCH_3$ | S | |
| 3.064 | H | H | $OCH_3$ | $SCH_3$ | S | |
| 3.065 | H | H | $OCH_3$ | $OC_3H_7(i)$ | S | |
| 3.066 | H | H | $HN-CH_3$ | $CH_3$ | S | |
| 3.067 | H | H | $HN-CH_3$ | $OCH_3$ | S | |
| 3.068 | H | H | $HN-CH_3$ | $OC_2H_5$ | S | |
| 3.069 | H | H | $N(CH_3)_2$ | $CH_3$ | S | |

TABLE 3-continued

Compounds of the formula Ib:

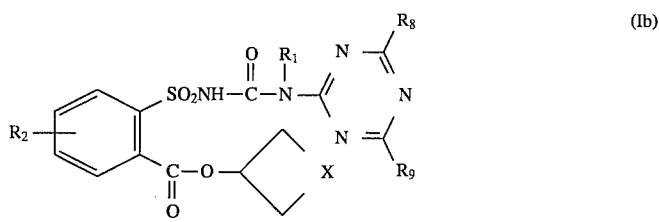

| Comp. No. | R₁ | R₂ | R₈ | R₉ | X | m.p. [°C.] |
|---|---|---|---|---|---|---|
| 3.070 | H | H | N(CH₃)₂ | OCH₃ | S | |
| 3.071 | H | H | C₂H₅ | OCH₃ | S | |
| 3.072 | H | H | CH₂F | OCH₃ | S | |
| 3.073 | H | H | CH₃ | OCH₂CF₃ | S | |
| 3.074 | H | H | OCH₃ | OCH₂CF₃ | S | |
| 3.075 | H | H | N(CH₃)₂ | OCH₂CF₃ | S | |
| 3.076 | H | H | CF₃ | OCH₃ | S | |
| 3.077 | H | H | OCH₃ | OCH₂CH₂OCH₃ | S | |
| 3.078 | CH₃ | H | CH₃ | OCH₃ | S | |
| 3.079 | CH₃ | H | OCH₃ | OCH₃ | S | |
| 3.080 | H | 5-Cl | CH₃ | OCH₃ | S | |
| 3.081 | H | 5-F | CH₃ | OCH₃ | S | |
| 3.082 | H | 6-Cl | CH₃ | OCH₃ | S | |
| 3.083 | H | 6-F | CH₃ | OCH₃ | S | |
| 3.084 | H | 5-CF₃ | CH₃ | OCH₃ | S | |
| 3.085 | H | 5-OCH₃ | CH₃ | OCH₃ | S | |
| 3.086 | H | 5-NO₂ | CH₃ | OCH₃ | S | |
| 3.087 | H | 5-C≡CH | CH₃ | OCH₃ | S | |
| 3.088 | H | 5-CH=CH—CF₃ | CH₃ | OCH₃ | S | |
| 3.089 | H | 5-CH₃ | CH₃ | OCH₃ | S | |
| 3.090 | H | 5-OCH₂CH₂Cl | CH₃ | OCH₃ | S | |
| 3.091 | H | 5-OCHF₂ | CH₃ | OCH₃ | S | |
| 3.092 | H | 3-Cl | CH₃ | OCH₃ | S | |
| 3.093 | H | 3-F | CH₃ | OCH₃ | S | |
| 3.094 | H | H | CH₃ | OCH₃ | SO | |
| 3.095 | H | H | OCH₃ | OCH₃ | SO | |
| 3.096 | H | H | CH₃ | OCH₃ | SO₂ | |
| 3.097 | H | H | OCH₃ | OCH₃ | SO₂ | |
| 3.098 | H | H | OC₂H₅ | cyclopropyl | S | |
| 3.099 | H | H | OC₂H₅ | cyclopropyl | SO₂ | |
| 3.100 | H | 5-CH₂—CH₂—CF₃ | CH₃ | OCH₃ | S | |
| 3.101 | H | 5-OCH₂CH₂OCH₃ | CH₃ | OCH₃ | S | |
| 3.102 | H | 5-SCH₂CHF₂ | CH₃ | OCH₃ | S | |
| 3.103 | H | 5-OCH₂CH=CH₂ | CH₃ | OCH₃ | S | |
| 3.104 | H | H | C₃H₇(i) | OCH₃ | S | |
| 3.105 | H | 6-CH₃ | N(CH₃)₂ | OCH₂CF₃ | O | |
| 3.106 | H | 5-C≡CCH₃ | OCH₃ | CH₃ | O | |
| 3.107 | H | H | OCH₃ | C₂H₅ | O | |
| 3.108 | H | H | OC₂H₅ | OCH₂CH₃ | O | |
| 3.109 | H | H | OCH₃ | cyclopropyl | O | |
| 3.110 | H | H | OC₂H₅ | N(CH₃)₂ | O | |
| 3.111 | H | H | OCH₃ | OCH₂CH₂Cl | O | |
| 3.112 | H | 4-OCH₃ | OCH₃ | CH₃ | O | |
| 3.113 | H | 5-OCH₂CH₂Cl | OCH₃ | CH₃ | O | |
| 3.114 | H | 6-CH₂F | OCH₃ | CH₃ | O | |
| 3.115 | H | 5-CH₂CH₃ | OCH₃ | CH₃ | O | |

TABLE 4

Compounds of the formula Ic:

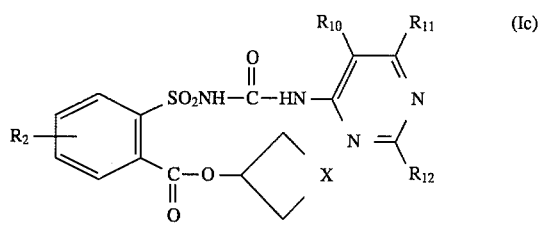

| Comp. No. | $R_2$ | $R_{10}$ | $R_{11}$ | $R_{12}$ | X | m.p. [°C.] |
|---|---|---|---|---|---|---|
| 4.001 | H | $CH_3$ | $CH_3$ | $OCH_3$ | O | |
| 4.002 | H | $CH_3$ | $OCH_3$ | $OCH_3$ | O | 185–187° |
| 4.003 | H | $CH_3$ | $OCH_3$ | $OC_2H_5$ | O | |
| 4.004 | H | $CH_3$ | $SCH_3$ | $OCH_3$ | O | |
| 4.005 | H | $CH_3$ | $OC_2H_5$ | $OCH_3$ | O | |
| 4.006 | H | $CH_3$ | Cl | $OCH_3$ | O | |
| 4.007 | H | $CH_3$ | F | $OCH_3$ | O | |
| 4.008 | H | Cl | $CH_3$ | $OCH_3$ | O | |
| 4.009 | H | Cl | $OCH_3$ | $OCH_3$ | O | 197–198° |
| 4.010 | H | F | $CH_3$ | $OCH_3$ | O | |
| 4.011 | H | $CF_3$ | $CH_3$ | $OCH_3$ | O | |
| 4.012 | H | $OCH_3$ | $CH_3$ | $OCH_3$ | O | |
| 4.013 | H | $SCH_3$ | $CH_3$ | $OCH_3$ | O | |
| 4.014 | H | $SOCH_3$ | $CH_3$ | $OCH_3$ | O | |
| 4.015 | H | $SO_2CH_3$ | $CH_3$ | $OCH_3$ | O | |
| 4.016 | H | CN | $CH_3$ | $OCH_3$ | O | |
| 4.017 | H | $OC_2H_5$ | $CH_3$ | $OCH_3$ | O | |
| 4.018 | H | $CH_3$ | $CH_3$ | $OCH_3$ | S | |
| 4.019 | H | $CH_3$ | $OCH_3$ | $OCH_3$ | S | |
| 4.020 | H | Cl | $CH_3$ | $OCH_3$ | S | |
| 4.021 | H | Cl | $OCH_3$ | $OCH_3$ | S | |
| 4.022 | H | F | $CH_3$ | $OCH_3$ | S | |
| 4.023 | H | H | $OCH_3$ | $OCH_3$ | S | |
| 4.024 | H | H | $OCH_3$ | $OCH_3$ | O | |
| 4.025 | H | $CH_3$ | $OCH_3$ | $OCH_3$ | SO | |
| 4.026 | H | $CH_3$ | $CH_3$ | $OCH_3$ | $SO_2$ | |
| 4.027 | H | $CH_3$ | $OCH_3$ | $OCH_3$ | $SO_2$ | |
| 4.028 | H | Cl | $OCH_3$ | $OCH_3$ | $SO_2$ | |
| 4.029 | 5-F | $CH_3$ | $CH_3$ | $OCH_3$ | O | |
| 4.030 | 5-Cl | $CH_3$ | $CH_3$ | $OCH_3$ | O | |
| 4.031 | H | $CF_3$ | $CH_3$ | $OCH_3$ | S | |
| 4.032 | H | $OCH_3$ | $CH_3$ | $OCH_3$ | S | |

TABLE 5

Compounds of the formula Id:

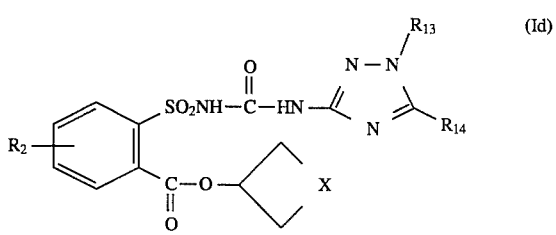

| Compound No. | $R_2$ | $R_{13}$ | $R_{14}$ | X | Melting point [°C.] |
|---|---|---|---|---|---|
| 5.001 | H | $CH_3$ | $CH_3$ | O | |
| 5.002 | H | $CH_3$ | $OCH_3$ | O | |
| 5.003 | H | $CH_3$ | Cl | O | |
| 5.004 | H | $CH_3$ | $OCHF_2$ | O | |
| 5.005 | H | $C_2H_5$ | $OCH_3$ | O | |
| 5.006 | H | $CH_3$ | $OC_2H_5$ | O | |
| 5.007 | H | $CH_3$ | $CH_3$ | S | |
| 5.008 | H | $CH_3$ | $OCH_3$ | S | |

TABLE 5-continued

Compounds of the formula Id:

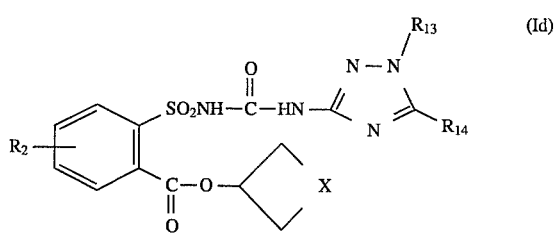

| Compound No. | $R_2$ | $R_{13}$ | $R_{14}$ | X | Melting point [°C.] |
|---|---|---|---|---|---|
| 5.009 | H | $CH_3$ | Cl | S | |
| 5.011 | H | $CH_3$ | $CH_3$ | SO | |
| 5.012 | H | $CH_3$ | $OCH_3$ | SO | |
| 5.013 | H | $CH_3$ | $CH_3$ | $SO_2$ | |
| 5.014 | H | $CH_3$ | $CH_3$ | $SO_2$ | |
| 5.015 | 5-F | $CH_3$ | $OCH_3$ | O | |
| 5.016 | 5-Cl | $CH_3$ | $OCH_3$ | O | |

Formulation Examples for Active Ingredients of the Formula I (%=per cent by Weight)

| 1. Wettable powder | a) | b) | c |
|---|---|---|---|
| Active ingredient according to Tables 2–5 | 20% | 50% | 0.5% |
| Sodium lignin sulfonate | 5% | 5% | 5 |
| Sodium lauryl sulfate | 3% | — | —% |
| Sodium diisobutylnaphthalenesulfonate | — | — | 6% 6% |
| Octylphenol polyethylene glycol ether (7–8 mol of ethylene oxide) | — | 2% | 2 |
| Highly disperse silicic acid | 5% | 27% | 27% |
| Kaolin | 67% | —% | — |
| Sodium chloride | — | — | 59.5% |

The active ingredient is mixed thoroughly with the additives and the mixture is ground thoroughly in a suitable mill. Wettable powders which can be diluted with water to give suspensions of any desired concentration are obtained.

| 2. Emulsion concentrates | a) | b) |
|---|---|---|
| active ingredient according to Tables 2–5 | 10% | 1% |
| Calcium dodecylbenzenesulfonate | 3% | 3% |
| Octylphenol polyethylene glycol ether (4–5 mol of ethylene oxide) | 3% | 3% |
| Castor oil polyethylene glycol ether (36 mol of ethylene oxide) | 4% | 4% |
| Cyclohexanone | 30 | 10% |
| Xylene mixture | 50% | 79% |

Emulsions of any desired concentration can be prepared from such concentrates by dilution with water.

| Dusts | a) | b) |
|---|---|---|
| Active ingredient according to Tables 2–5 | 0.1% | 1% |
| Talc | 99.9% | — |
| Kaolin | — | 99% |

Ready-to-use dusts are obtained by intimate mixing of the carriers with the active ingredient.

| 4. Extruded granules | a) | b) |
|---|---|---|
| Active ingredient according to Tables 2–5 | 10% | 1% |
| Sodium ligninsulfonate | 2% | 2% |
| Carboxymethylcellulose | 1% | 1% |
| Kaolin | 87% | 96% |

The active ingredient is mixed with the additives and the mixture is ground and moistened with water. This mixture is extruded and the extrudate is then dried in a stream of air.

| 5. Coated granules | |
|---|---|
| Active ingredient according to Tables 2–5 | 3% |
| Polyethylene glycol (molecular weight 200) | 3% |
| Kaolin | 94% |

The finely ground active ingredient is applied uniformly to the kaolin, which has been moistened with polyethylene glycol, in a mixer. Dust-free coated granules are obtained in this manner.

| 6. Suspension concentrate | a) | b) |
|---|---|---|
| active ingredient according to Tables 2–5 | 5% | 40% |
| Ethylene glycol | 10% | 10% |
| Nonylphenol polyethylene glycol ether (15 mol of ethylene oxide) | 1% | 6% |
| Sodium ligninsulfonate | 5% | 10% |
| Carboxymethylcellulose | 1% | 1% |
| 37% aqueous formaldehyde solution | 0.2% | 0.2% |
| Silicone oil in the form of a 75% aqueous emulsion | 0.8% | 0.8% |
| Water | 77% | 32% |

The finely ground active ingredient is intimately mixed with the additives. A suspension concentrate is thus obtained, from which suspensions of any desired concentration can be prepared by dilution with water.

| 7. Salt solution | |
|---|---|
| Active ingredient according to Tables 2–5 | 5% |
| Isopropylamine | 1% |
| Octylphenol polyethylene glycol ether (78 mol of ethylene oxide) | 91% |

The compounds of the formula I are employed in unchanged form or, preferably, as compositions together with the auxiliaries customary in formulation technology, and are therefore processed in a known manner for example to emulsion concentrates, directly sprayable or dilutable solutions, dilute emulsions, wettable powders, soluble powders, dusts, granules and also capsules in, for example, polymeric substances. The methods of use, such as spraying, misting, dusting, scattering or pouring, like the nature of the compositions, are chosen according to the desired effets and the given circumstances.

BIOLOGICAL EXAMPLES

Example B1

Herbicidal Action before Emergence of the Plants

Plastic pots are filled with expanded vermiculite (density: 0.135 g/cm$^3$, water adsorption capacity: 0.565 l/l). After saturation of the non-adsorbent vermiculite with an aqueous active ingredient emulsion in deionised water which contains the active ingredients in a concentration of 70.8 ppm, seeds of the following plants are sown on the surface: Nasturtium officinalis, Agrostis tenuis, Stellaria media and Digitaria sanguinalis. The test vessels are then kept in a climatically controlled chamber at a temperature of 20° C., an illumination of about 20 klux and a relative atmospheric humidity of 70%. During a germination phase of 4 to 5 days, the pots are covered with transparent material, to increase the local atmospheric humidity, and watered with deionised water. After the 5th day, 0.5% of a commercially available liquid fertiliser is added to the watering water. The test is evaluated 12 days after sowing and the action on the test plants is rated according to the following scale:

1: plants not germinated or died off completely
2–3: very severe action
4–6: moderate action
7–8: weak action
9: no action (as untreated control)

TABLE B1

Preemergence action:
Concentration of the active ingredient emulsion: 70.8 ppm
Test plants: Nasturtium Stellaria Agrostis Digitaria

| Active ingredient No. | | | | |
|---|---|---|---|---|
| 2.001 | 3 | 3 | 1 | 3 |
| 2.002 | 3 | 2 | 2 | 3 |
| 2.003 | 1 | 2 | 1 | 3 |
| 2.093 | 2 | 3 | 3 | 3 |
| 3.003 | 3 | 2 | 1 | 3 |
| 3.011 | 1 | 2 | 1 | 2 |

Example B2

Postemergence Herbicidal Action (Contact Herbicide)

After emergence (in the 4- to 6-leaf stage), a number of weed plant, both monocotyledonous and dicotyledonous, were sprayed with an aqueous active ingredient dispersion in a dosage of 8–500 g of active substance per hectare, and these were kept at 24°–26° C. and 45–60% relative atmospheric humidity. The test is evaluated 15 days after the treatment.

After 3 weeks, the herbicidal action is rated with a nine-level (1=complete destruction, 9=no action) rating scale in comparison with an untreated control group. Ratings of 1 to 4 (in particular 1 to 3) indicate a good to very good herbicidal action. Ratings of 6 to 9 (in particular 7 to 9) indicate a good tolerance (in particular by crop plants).

The compounds of the formula I show a potent herbicidal action in this test.

Example B3

Herbicidal Action for Paddy Rice

The aquatic weeds *Echinochloa crus galli* and *Monocharia vag.* are sown in plastic beakers (60 cm$^2$ surface area, 500 ml volume). After sowing, the beakers are filled with water to the soil surface. 3 days after sowing, the water level is increased to slightly above the soil surface (3–5 mm). The application is carried out 3 days after sowing by spraying the test substances onto the vessels. The dose used corresponds to an amount of active ingredient of 8–500 g of active substance per hectare. The plant beakers are then placed in a greenhouse under optimum growing conditions for the rice weeds, i.e. at 25°–30° C. and high atmospheric humidity.

The tests are evaluated 3 weeks after the application. The compounds of the formula I damage the weeds in this test.

What is claimed is:

1. A compound of the formula I

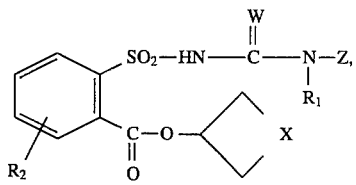

(I)

in which X is oxygen, sulfur, SO or $SO_2$; W is oxygen or sulfur, $R_1$ is hydrogen or methyl; $R_2$ is hydrogen, fluorine, chlorine, bromine, iodine, $(X)_n R_3$, $NO_2$, $NR_4 R_5$, —C≡$CR_6$,

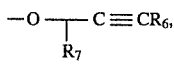

or cyano; n is the number 0 or 1; Z is

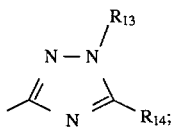

$R_{13}$ is $C_1$–$C_3$alkyl; and $R_{14}$ is $C_1$–$C_3$alkyl, $C_1$–$C_3$alkoxy, chlorine or $OCHF_2$; or a salt of these compounds.

2. A compound of the formula I according to claim 1, in which W is oxygen.

3. A compound of the formula I according to claim 2, in which X is sulfur; $R_2$ is hydrogen, fluorine, chlorine, $OCH_3$, $OCHF_2$, methyl or methylthio.

4. A compound of the formula I according to claim 3, in which X is sulfur; $R_2$ is hydrogen.

5. A herbicidal and plant growth-inhibiting composition which contains one or more sulfonylureas and -thioureas of the formula I according to claim 1.

6. A composition according to claim 5, which contains between 0.1% and 95% of the active ingredient of the formula I according to claim 1.

7. A method for control of undesirable plant growth, which comprises applying an effective amount of an active ingredient of the formula I according to claim 1 or a composition containing this active ingredient to the plants or their environment.

8. The method according to claim 7, wherein an amount of active ingredient of between 0.001 and 2 kg per hectare is applied.

9. A method of inhibiting plant growth, which comprises applying an effective amount of an active ingredient of the formula I according to claim 1 or a composition containing this active ingredient to the plants or their environment.

10. The method according to claim 7 for selective pre- or postemergence control of weeds in crops of useful plants.

* * * * *